United States Patent
Zeng et al.

(10) Patent No.: US 10,753,831 B2
(45) Date of Patent: Aug. 25, 2020

(54) METHOD FOR DETECTION OF AIR-WATER EXCHANGE FLUX

(71) Applicant: GUANGZHOU INSTITUTE OF GEOCHEMISTRY, CHINESE ACADEMY OF SCIENCES, Guangzhou (CN)

(72) Inventors: Eddy Y. Zeng, Guangzhou (CN); Chenchou Wu, Guangzhou (CN); Fengchang Wu, Guangzhou (CN); Lianjun Bao, Guangzhou (CN)

(73) Assignee: GUANGZHOU INSTITUTE OF GEOCHEMISTRY, CHINESE ACADEMY OF SCIENCES, Guangzhou, Guangzhou Prov. (CN)

( * ) Notice: Subject to any disclaimer, the term of this patent is extended or adjusted under 35 U.S.C. 154(b) by 164 days.

(21) Appl. No.: 15/566,420

(22) PCT Filed: Jun. 12, 2015

(86) PCT No.: PCT/CN2015/081377
§ 371 (c)(1),
(2) Date: Feb. 15, 2018

(87) PCT Pub. No.: WO2016/165207
PCT Pub. Date: Oct. 20, 2016

(65) Prior Publication Data
US 2018/0149558 A1    May 31, 2018

(30) Foreign Application Priority Data
Apr. 16, 2015    (CN) .......................... 2015 1 0182147

(51) Int. Cl.
*G01N 1/10*    (2006.01)
*G01N 33/18*    (2006.01)
(Continued)

(52) U.S. Cl.
CPC ............... *G01N 1/10* (2013.01); *G01N 13/00* (2013.01); *G01N 33/0027* (2013.01);
(Continued)

(58) Field of Classification Search
CPC .. G01N 1/10; G01N 33/1886; G01N 33/0027; G01N 13/00; G01N 2001/1031; G01N 1/16
See application file for complete search history.

(56) References Cited

U.S. PATENT DOCUMENTS

| 8,511,184 B2 * | 8/2013 | Voll | .......................... G01N 1/16 |
| | | | 73/863.81 |
| 2007/0113687 A1 * | 5/2007 | Sauter | ...................... G01N 1/12 |
| | | | 73/864.66 |

(Continued)

FOREIGN PATENT DOCUMENTS

CN    101608982    * 12/2009    ............... G01N 1/10

*Primary Examiner* — Daniel S Larkin
*Assistant Examiner* — Anthony W Megna Fuentes
(74) *Attorney, Agent, or Firm* — Craft Chu PLLC; Andrew W. Chu

(57) ABSTRACT

Disclosed is a method for detection of air-water exchange flux of organic contaminants, which passively and continuously collects contaminants at consecutive points close to a sea surface microlayer, acquires the freely dissolved concentration at the consecutive points of the air and water body close to a water body surface microlayer, and obtains the air-water exchange flux of the contaminants through fitting a self-developed model, wherein the consecutive points include a plurality of sampling points along a height direction above an air-water interface and a plurality of sampling points along a depth direction below the air-water interface. The present invention can be applied to determine the air-water body exchange flux of organic contaminants.

10 Claims, 2 Drawing Sheets

(51) Int. Cl.
*G01N 33/00* (2006.01)
*G01N 13/00* (2006.01)
*G01N 1/16* (2006.01)

(52) U.S. Cl.
CPC ..... *G01N 33/1826* (2013.01); *G01N 33/1886* (2013.01); *G01N 1/16* (2013.01); *G01N 2001/1025* (2013.01); *G01N 2001/1031* (2013.01)

(56) References Cited

U.S. PATENT DOCUMENTS

| | | | | |
|---|---|---|---|---|
| 2012/0180578 A1* | 7/2012 | Zeng | ................. | E02D 1/06 |
| | | | | 73/863.23 |
| 2014/0102182 A1* | 4/2014 | Halden | ................. | B01D 35/26 |
| | | | | 73/61.73 |
| 2014/0165712 A1* | 6/2014 | Zeng | ................. | G01N 1/10 |
| | | | | 73/64.56 |

* cited by examiner

METHOD FOR DETECTION OF AIR-WATER EXCHANGE FLUX

FIELD OF THE INVENTION

The present invention relates to the field of environment, and more particularly, to a method for detection of air-water exchange flux.

BACKGROUND OF THE INVENTION

The surface microlayer (Surface Microlayer, SML) of a water body is a thin layer between the air and the water body, and is the only road for exchange of substances in the air-water interface. That is, from a microscopic aspect, almost all substances enter or leave the water body through a boundary of the water body surface microlayer for air-water exchange and convert in the surface microlayer. The water surface microlayer has special physical-chemical-biological properties, and has direct and important influences on the biogeochemical cycle of the water body, the air-water exchange flux of substances and even the climate, etc.

The composition and property of the water body surface microlayer are associated with different samplers and the thickness of the surface layer that is taken. Normal samplers include various sieve and rotary drum type surface layer samplers; moreover, the surface layer samples may also be collected through a manner of vertically getting water from the water using a glass plate. The methods above are generally called as active methods, and the thicknesses of the surface layers obtained are around 100 microns mostly. Wherein, the sieve and glass plate sampling manners are suitable for rivers, lakes and offshore regions; because the concentration of the contaminants is low and the detection line is high, a relatively large amount of sample volume is required, so that a large number of labour power and time are required. The rotary drum surface layer sampler can save the labour power and time, but the cost thereof is high and the volume thereof is relatively large; therefore, it is suitable for correlational studies in ocean regions.

However, the results obtained through the active method are instantaneous concentrations mostly (short time concentration), and related results of geochemical cycle and air-water exchange flux in a relatively long time period cannot be obtained, which is not beneficial for developing studies on an air-water heterogeneous interface (phase transformation). Meanwhile, the dissolved concentration of the water body obtained needs to be corrected, so as to obtain the freely dissolved concentration.

Sampling solutions in the correlational studies about the air-water exchange flux include (1) respectively sampling one point in the air and one point in the water body to conduct studies about exchange of substance and flux; however, in this method, there is no uniform specification for sampling height (defined by the sampling condition) in the academic circle; and (2) setting a plurality of sampling heights in the atmospheric layer to fit the results. This method infers atmospheric precipitation or water body volatilization according to the concentration changes of each point; however, in this method, the influences of the water body surface microlayer on the air-water body exchange are not taken into consideration, and the air-water body exchange may be overrated/underrated.

SUMMARY OF THE INVENTION

In order to overcome the foregoing technical problems, the object of the present invention is to provide an air-water exchange flux detection method, which can obtain the air-water exchange flux of target contaminants more accurately.

The present invention employs a technical solution as follows:

a method for detection of air-water exchange flux includes the steps of passively and continuously collecting contaminants at consecutive points close to a sea surface microlayer, acquiring the freely dissolved concentration at the consecutive points of the air and water body close to a water body surface microlayer, and obtaining the air-water exchange flux of the contaminant through fitting, wherein the consecutive points include a plurality of sampling points in the air along a height direction and a plurality of sampling points in the water body along a depth direction.

As a further improvement of the present invention, the distances between the adjacent sampling points in the air are all greater than the distance between a air-water interface and any sampling point in the air; and the distances between the adjacent sampling points in the water body are all greater than the distance between the air-water interface and any sampling point in the water body.

As a further improvement of the present invention, sampling units are respectively located and placed at each consecutive point close to the sea surface microlayer, and the contaminants at the location are continuously absorbed by absorption phases of the sampling units, so as to passively collect the contaminants.

As a further improvement of the present invention, the absorption phases are enabled to absorb a certain amount of reference solution before the sampling units are placed, and the reference solution is a standard solution containing a reference similar to the contaminants in terms of physico-chemical property.

As a further improvement of the present invention, the sampling units are relatively fixed and form a layered body, and the body floats on the water surface through buoyancy, so that parts of the sampling units are exposed in the air, and the rest sampling units are located in the water body.

As a further improvement of the present invention, the method includes the steps of eluting the contaminants from each sampling unit, obtaining the freely dissolved concentration of the contaminants in the corresponding sampling points of the water body or the air through calculation, fitting the concentration values at the adjacent height or depth, averaging the concentration values of the sampling points in the air and water body closest to the air-water interface and taking the averaged value as the freely dissolved concentration of the air-water interface, thus converting to the time weighted average exchange flux of the air-water interface.

As a further improvement of the present invention, the sampling units comprise absorption phases, filter membranes disposed at the two sides of the absorption phases and clamping plates covering the filter membranes.

As a further improvement of the present invention, wind-proof and rainproof measures are taken to protect the sampling units exposed in the air.

The present invention has the advantageous effects that: the present invention sufficiently considers the influences of the water body surface microlayer on air-water body exchange, collects the contaminants at the consecutive points close to the sea surface microlayer through a passive sampling method, acquires the freely dissolved concentration at the consecutive points of the air and water body close to a water body surface microlayer, and obtains the air-water exchange flux of the related contaminants.

BRIEF DESCRIPTION OF THE DRAWINGS

The present invention will be described with reference to the drawings and embodiments hereinafter.

DETAILED DESCRIPTION OF THE EMBODIMENTS

A method for detection of air-water exchange flux employs a principle of passively and continuously collecting contaminants at consecutive points close to a sea surface microlayer, acquiring the freely dissolved concentration at the consecutive points of the air and water body close to a water body surface microlayer and obtaining the air-water exchange flux of the contaminant through fitting. The consecutive points above refer to a plurality of sampling points in the air along a height direction and a plurality of sampling points in the water body along a depth direction.

Figure 1:
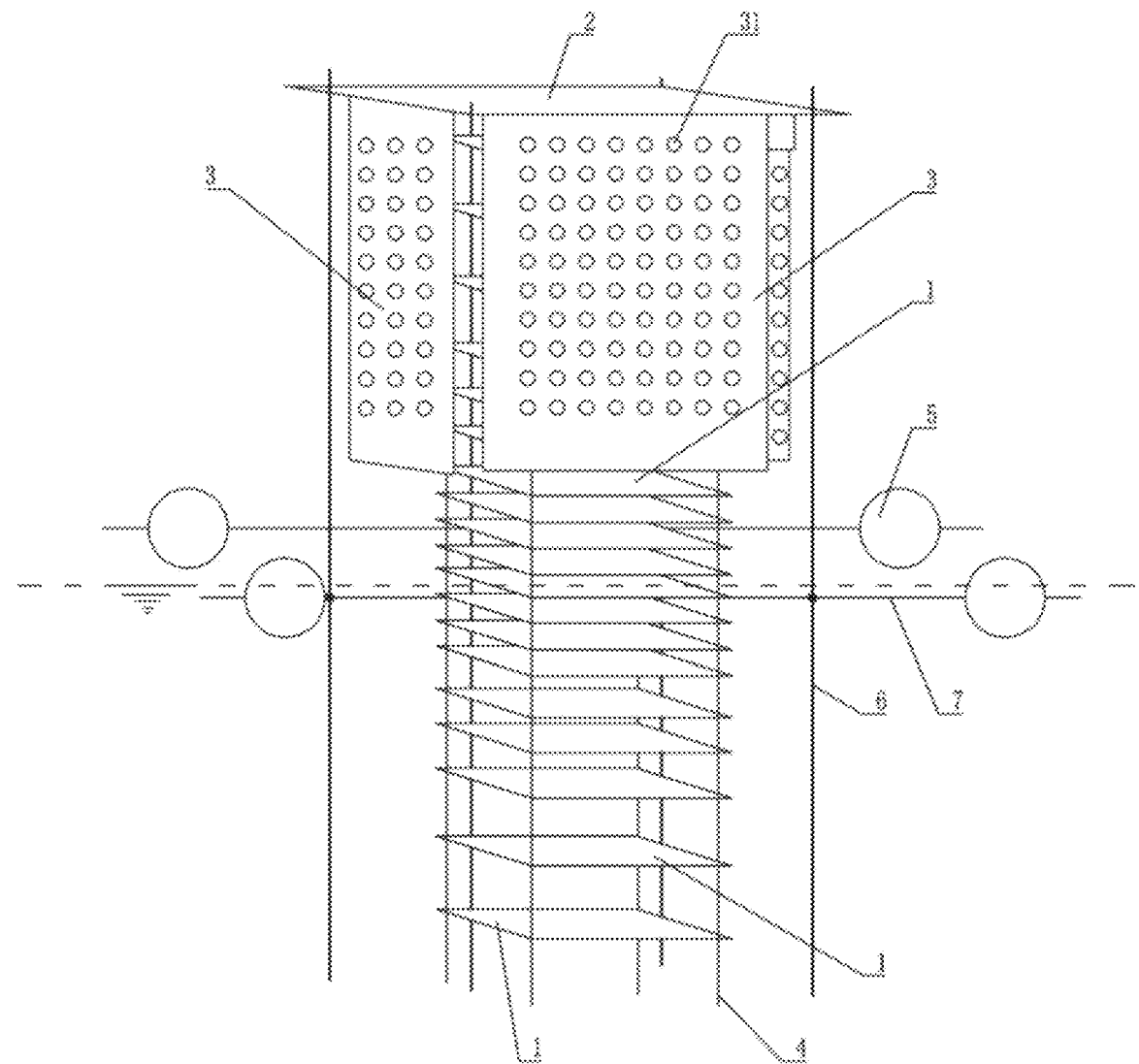
FIG. 1 is a structure diagram of a body formed by sampling units.

In one embodiment, a passive sampling device is used while implementing the detection method. As shown in FIG. 1, the passive sampling device includes a body, wherein the body is composed of sampling units 1, buoyancy units, a waterproof shading unit and a supporting unit.

Figure 2:
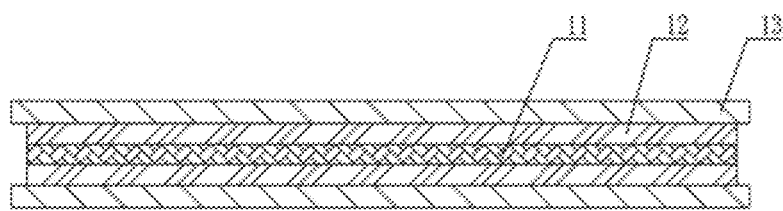
FIG. 2 is a structure diagram of the sampling units.

Wherein, a plurality of sampling units 1 are provided, and the plurality of sampling units 1 are arranged along a vertical direction to form a multilayer structure. To be specific, as shown in FIG. 2, each sampling unit 1 is composed of a horizontal adsorption film 11, filter membranes 12 disposed at the two sides of the adsorption film 11 and a clamping plate 13 covering the filter membranes 12, wherein the adsorption film 11, a strainer and the clamping plate 13 are connected into a flake-like structure through screw or rivet or pin shaft. The adsorption film 11, serving as an adsorption phase, absorbs the contaminants from the water body or air. The filter membrane 12 plays a role of filtering granules. The clamping plate 13 can play a role of supporting and protecting the adsorption film 11 and the filter membrane 12, ensure that the sampling units are under a horizontal state, so as to improve the data accuracy. Generally, the adsorption film 11 is a polyethylene adsorption film. Certainly, the absorption phase may not employ the form of adsorption film as well, and the filter membrane 12 is a fiberglass filter membrane.

As shown in FIG. 1, the above buoyancy units are four floating balls 5, and the body, when in use, floats on the water surface by means of the floating balls. The four floating balls 5 are relatively fixed with the sampling units 1. Seen from the height direction, the plane where the four floating balls 5 locate is approximately in the middle of the body; therefore, under the effect of buoyancy, a plurality of sampling units 1 are exposed in the air, so as to form an air collection portion; because the sampling units at the air collection portion are disposed along the height direction, the contaminants at each consecutive point close to the sea surface microlayer in the air can be continuously absorbed and collected; the rest sampling units are soaked in the water body so as to form a water body collection portion; because the sampling units in the water body collection portion are disposed along the depth direction, the contaminants at each consecutive point close to the sea surface microlayer in the water body can be continuously absorbed and collected.

The sampling unit undermost the air collection portion is located above a liquid level (shown by a dotted line in FIG. 1), and is closest to the liquid level; it is assumed that the distance thereof is A; on the contrary, the sampling unit on the top of the water body collection portion is located above the liquid level, and is closest to the liquid level; it is assumed that the distance thereof is B; preferably, the arrangement of the position of the floating ball 5 enables A to be equal to B as much as possible, then the data measured at this position is more accurate for the calculation of the air-water exchange flux.

When collecting contaminants, the sampling units 1 and the body are approximately static to the water body surface microlayer, so that the absorption phases can continuously absorb and collect the contaminants at the same position; therefore, the method and device of the embodiment can collect the contaminants passively.

When collecting the contaminants, two conditions shall be satisfied: the distances between the adjacent sampling points in the air are all greater than the distance between a air-water interface and any sampling point in the air; and the distances between the adjacent sampling points in the water body are all greater than the distance between the air-water interface and any sampling point in the water body. In terms of sampling devices, a high resolution is required at points close to the interface; therefore, the distance between two adjacent sampling points close to the interface is minimum, and there is no special requirement on the distance between two adjacent sampling points far from the interface, and this distance can change properly. Meanwhile, the number of the sampling units in the air collection portion is no less than 3, while the number of the sampling units in the water body collection portion is no less than 3 as well.

When collecting the contaminants, the air collection portion is exposed in the air, and the sampling units will be influenced by wind and rain when the device is collecting data; therefore, it is desirable to take windproof and rainproof measures to protect the sampling units. To be specific, a waterproof shading unit is employed to cover outside the air collection portion.

The waterproof shading unit includes a cover plate 2 and side plates 3. The cover plate 2 is located just above the air collection portion, the side plates 3 surround the periphery of the air collection portion and are connected below the cover plate 2, so that the cover plate 2 and the side plates 3 form a housing with an opening at the bottom, wherein the housing can minimize the influences of rain and wind from the top and lateral sides on the sampling units 1. Air vents 31 are also densely arranged on the side plate 3, and these air vents 31 shall satisfy the need that the gas carrying the contaminants can enter; however, the existence of these air vents 31 cannot affect the windproof demand.

The supporting unit in the device is mainly configured for connection and localization between the parts and units in the body. As shown in FIG. 1, the supporting unit includes four supporting rods 4, wherein each supporting rod 4 is connected with one corner of the sampling unit 1, so that the sampling units 1 are connected in series into a columnar shape. The top portions of the above supporting rods 4 are connected to the bottom end surface of the cover plate 2, and all the sampling units 1 are indirectly supported by the cover plate 2. The four corners of the cover plate 2 are also connected with a vertical connecting rod 6, and these connecting rods 6 downwardly extend till the bottom portion of the water body collection portion. The four floating balls 5 are fixed with the connecting rods 6 through cross rods 7 respectively.

The process of the method according to the embodiment will be explained hereinafter.

1. Before placing the passive sampling device, each absorption phase is placed into a standard solution containing PRC [reference is similar to a target object in terms of physicochemical property (performance reference compound, PRC)], so that the absorption phases absorb a certain amount of PRC, then the absorption phases are placed into an environment to be sampled for sampling.

2. The device continuously takes samples in the environment, wherein the sampling time is t, and t is determined according to the contaminants and absorption phases; if the absorption phase is a PE membrane, then t is 15-20 days at least, and it may possibly be up to a half year.

3. Afterwards, the contaminants are eluted (extracted using an organic solvent) from each sampling unit, and the concentration of the absorption phase is converted into freely dissolved concentration through calculation. The details are as follows:

$$C_{W(A)} = \frac{C_S}{K_{SW(A)}(1-f)} \quad (1)$$

The concentration of the contaminants at a certain height/depth in the water body or air is obtained through the formula (1);

$C_S$, unit in g/kg, is the concentration of the contaminants on the absorption phase;

$K_{SW}$, unit in (g/kg)/(g/L), wherein $K_{SW}$ is an absorption phase-water distribution constant, and $K_{SA}$ is an absorption phase-air distribution constant;

$C_W$, unit in ng/L or pg/L, is the concentration of the contaminants in the water body/pore water;

$C_A$, unit in ng/m$^3$ or pg/m$^3$, is the concentration of the contaminants in the air; and f is a specific value.

It is provided that the absorption process of the contaminants with the water in the absorption phase is a first order kinetics process, and the concentration of the target object in the water body is unchanged, then the concentration ($C_S$) of the target object on the absorption phase at any time point (t) can be represented as:

$$C_w = \frac{C_{s(t)}}{(1 - e^{-k_e t}) \times K_{sorbent-water}} \quad (1\text{-}2)$$

Similarly, the desorption process of the PRC on the absorption phase can be represented as:

$$k_e = \ln\left(\frac{C^0_{s-PRC}}{C^t_{s-PRC}}\right) \times t^{-1} \quad (1\text{-}3)$$

Where, $C_{s-PRC}^0$ and $C_{s-PRC}^t$ are the primary concentration of the PRC on the absorption phase and the concentration of the PRC when the sampling time is t. By substituting the equation (1-3) into the equation (1-2), an equation (1-4) can be obtained:

$$C_w = \frac{C_{s(t)}}{\left(1 - \frac{C^t_{s-PRC}}{C^0_{s-PRC}}\right) \times K_{sorbent-water}} \quad (1\text{-}4)$$

That is, $$f = \frac{C^0_{s-PRC}}{C^t_{s-PRC}}.$$

Figure 3:
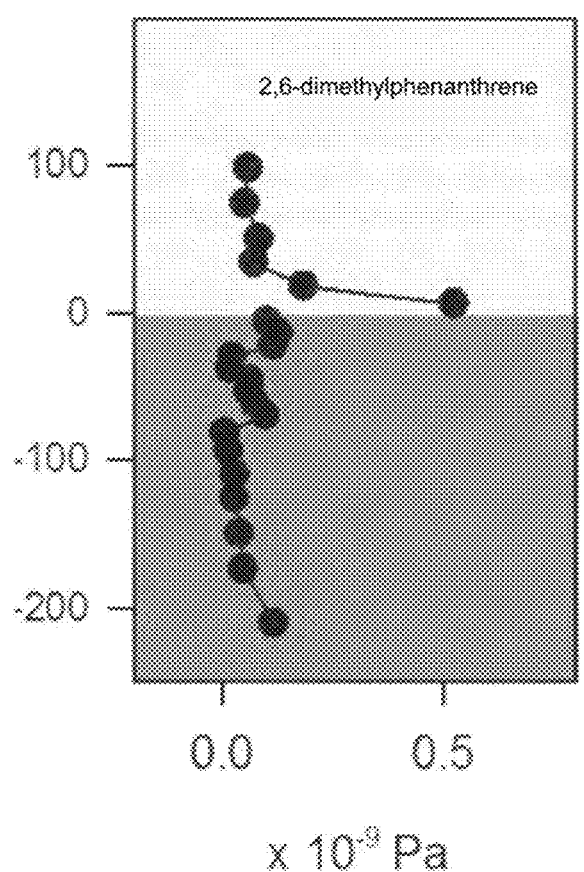
FIG. 3 is a curve showing freely dissolved concentration of each consecutive point close to a water body surface microlayer.

4. Those concentration values obtained at adjacent points at the height or depth direction among all the concentration values calculated in the third aspect are selected and connected into a line, then the concentration values of the sampling points in the air and in the water body closest to the liquid level are averaged and then served as the freely dissolved concentration $C_0$ of the air-water interface, which is as shown in FIG. 3. In FIG. 3, the contaminant is 2,6-dimethylphenanthrene, the portion above the coordinate scale 0 is an air phase, and the portion below the coordinate scale 0 is an aqueous phase.

5. The time weighted average exchange flux F of the air-water interface is calculated according to $C_0$, wherein the details are as follows:

The freely dissolved concentration (C) of the contaminant at points with any water depth in the water body can be represented as (Taylor expansion):

$$C = C_0(1 + a_1 z_w + a_2 z_w^2 + \ldots + a_n z_w^n) \quad (2)$$

Note: the formula is in the case that the medium is a water body. $C=C_0(1+a_1Z_w+a_2Z_w^2+\ldots+a_nZ_w^n)$ is a general form (i.e., general to other environment medium).

According to Fick's Law of Diffusion, F can be calculated as:

$$F = -D\frac{dC}{dz_w} \quad (3)$$

By substituting the equation (2) into the equation (3), it can be obtained:

$$F = -D\frac{dC}{dz_w} = -DC_0(a_1 + 2a_2 z_w + \ldots + na_n z_w^{n-1}) \quad (4)$$

When $Z_w=0$ (this is a air-water interface), the equation (4) can be converted as:

$$F = -DC_0 a_1 \quad (5)$$

The exchange flux in the formula (5) (F) is an instantaneous value. Actually, the concentration of an organic matter is determined by measuring the concentration of the contaminants contained in the absorption phase on the passive sampling device in a certain time period t. Then the flux in the time period t is the time weighted average exchange flux $\overline{F}$:

$$\overline{F} = -DC_0 \overline{a_1} \quad (6)$$

Wherein, the environmental concentration thereof in the time period t keeps unchanged or has small periodic fluctuation. In addition, the concentration obtained from the passive sampling method is a time weighted average concentration $\overline{C_w}$, which may also be represented by Taylor expansion as:

$$\overline{C_w} = \overline{C_0}(1 + a_1' z_w + a_2' z_w^2 + \ldots + a_n' z_w^n) \quad (7)$$

Because the environmental concentration keeps unchanged or has small periodic fluctuation, the let $\overline{C_0}=C_0$. Meanwhile, related parameters of $a_i'=1, 2, \ldots, n$) can be obtained through fitting, then the time weighted average exchange flux $\overline{F}$ is:

$$\overline{F} = -DC_0 a_1' \qquad (8)'$$

Through the formula (8), the time weighted average exchange flux $\overline{F}$ of the organic matter in the time period t can be obtained; wherein D is the diffusion rate constant of the organic matter; and related parameters of $a_i'$ (i=1, 2, ..., n) can be obtained through fitting.

In order to obtain the time weighted average exchange flux from the formula (8) $\overline{F}$, $\overline{a_1}$ has to be equal to $a_1'$.

While through defining, $\overline{C_w}$ can be expressed as:

$$\overline{C_w} = \frac{1}{t}\int C_w dt \qquad (9)$$

The equation (2) is substituted into the formula (9)

$$\overline{C_w} = \frac{1}{t}\int C_o(1 + a_1 z_w + a_2 z_w^2 + \ldots + a_n z_w^n)dt = \qquad (10)$$
$$C_o(1 + \overline{a_1} z_w + \overline{a_2} z_w^2 + \ldots + \overline{a_n} z_w^n)$$

Comparing the formula (7) with the formula (10), it can be obtained that $\overline{a_1} = a_1'$; similarly, $\overline{a_2} = a_2'$, $\overline{a_3} = a_3'$, ..., $\overline{a_n} = a_n'$. Wherein:

C: (contaminant) freely dissolved concentration;
$\overline{C_w}$: (the contaminant in the water body) time weighted average concentration;
$\overline{C_0}$: (the contaminant) time weighted average concentration at the interface;
$C_0$: (the contaminant) concentration at the interface;
F: (contaminant) exchange flux;
$\overline{F}$: (contaminant) time weighted average exchange flux;
$Z_w$: a certain point in the water depth;
i: a certain sampling point i;
D: (contaminant) diffusion rate constant;
t: time period, sampling period;

$$\frac{dC}{dz_w}$$

is (partial differential on mathematics, i.e., derivation of concentration to height); and dC is (contaminant) concentration at a certain sampling water depth $dz_w$;
∫ dt is (integral expression on mathematics); and
a, $\overline{a_1}$, $a_1'$, ... are all non-dimensional fitting constants, which are obtained by fitting the concentrations of multiple points obtained by the sampling device in the medium.

The above describes the preferred embodiments of the present invention merely, and is not intended to limit the protection scope of the present invention.

The invention claimed is:

1. A method for detection of air-water exchange flux, comprising:
   passively and continuously collecting contaminants at consecutive points located at a distance from a water body surface microlayer;
   acquiring freely dissolved concentration values of contaminants at the consecutive points of the air and a water body located at a distance from the water body surface microlayer; and
   obtaining the air-water exchange flux of the contaminants through fitting, wherein the consecutive points comprise a plurality of sampling points along a height direction above an air-water interface and a plurality of sampling points along a depth direction below the air-water interface.

2. The method for detection of air-water exchange flux according to claim 1, wherein distances between juxtaposed sampling points in the air are all greater than a distance between the air-water interface and a sampling point in the air closest to the air-water interface; and distances between juxtaposed sampling points in the water body are all greater than the distance between the air-water interface and a sampling point in the water body closest to the air-water interface.

3. The method for detection of air-water exchange flux according to claim 2, wherein sampling units are respectively located and placed at each consecutive point located at a distance from the water body surface microlayer, and the contaminants at each location are continuously absorbed by absorption phases of the sampling units, so as to passively collect the contaminants.

4. The air-water exchange flux detection method according to claim 2, wherein windproof and rainproof components are configured to protect the sampling units exposed in the air.

5. The method for detection of air-water exchange flux according to claim 1, wherein sampling units are respectively located and placed at each consecutive point located at a distance from the water body surface microlayer, and the contaminants at the location are continuously absorbed by absorption phases of the sampling units, so as to passively collect the contaminants.

6. The method for detection of air-water exchange flux according to claim 5, wherein the absorption phases are enabled to absorb a certain amount of reference solution before the sampling units are placed at their respective points, and the reference solution is a standard solution containing a reference having physicochemical properties.

7. The method for detection of air-water exchange flux according to claim 5, wherein the sampling units are relatively fixed to form a layered body, and the layered body floats on the water body surface through buoyancy, so that parts of the sampling units are exposed in the air, and the rest sampling units are located in the water body.

8. The method for detection of air-water exchange flux according to claim 5, comprising
   eluting the contaminants from each sampling unit,
   obtaining the freely dissolved concentration values of the contaminants in the corresponding sampling points of the water body or the air through calculation,
   fitting the concentration values obtained at the juxtaposed points at the height or depth direction,
   averaging the concentration values of the sampling points closest to the air-water interface in the air and the water body and
   taking the averaged value as the freely dissolved concentration values of the contaminants of the air-water interface, thus converting the freely dissolved concentration value to a time weighted average exchange flux of the air-water interface.

9. The air-water exchange flux detection method according to claim 5, wherein each sampling unit comprises an absorption phase, filter membranes disposed at the two sides of the absorption phase, and clamping plates covering the filter membranes.

10. The air-water exchange flux detection method according to claim 1, wherein windproof and rainproof components are configured to protect the sampling units exposed in the air.

* * * * *